US005932558A

United States Patent [19]
Cronstein et al.

[11] Patent Number: 5,932,558
[45] Date of Patent: Aug. 3, 1999

[54] ADENOSINE RECEPTOR AGONISTS FOR THE PROMOTION OF WOUND HEALING

[75] Inventors: Bruce N. Cronstein; Richard I. Levin, both of New York, N.Y.

[73] Assignee: New York University, New York, N.Y.

[21] Appl. No.: 08/712,942

[22] Filed: Sep. 13, 1996

Related U.S. Application Data

[63] Continuation of application No. 08/046,297, Apr. 15, 1993, abandoned.

[51] Int. Cl.$^6$ .................................................. A61K 31/70
[52] U.S. Cl. .............................................................. 514/46
[58] Field of Search .............................................. 514/46

[56] References Cited

U.S. PATENT DOCUMENTS

| | | | |
|---|---|---|---|
| 4,308,257 | 12/1981 | Caspe ...................................... | 424/180 |
| 4,456,596 | 6/1984 | Schafer ................................... | 424/180 |
| 4,705,758 | 11/1987 | Bruns . | |
| 4,897,394 | 1/1990 | Zimmerman . | |
| 4,968,697 | 11/1990 | Hutchison . | |
| 5,034,381 | 7/1991 | Hutchison . | |
| 5,063,233 | 11/1991 | Chen et al. . | |
| 5,069,895 | 12/1991 | Diamond et al. ........................ | 424/10 |
| 5,183,663 | 2/1993 | Greiner .................................... | 424/443 |
| 5,196,185 | 3/1993 | Silver et al. ............................. | 424/45 |

FOREIGN PATENT DOCUMENTS 8803147  5/1988  WIPO .

OTHER PUBLICATIONS

Barrington, W.W. et al., "Identification of the $A_2$ Adenosine Receptor Binding Subunit by Photoaffinity Crosslinking" *Proc Natl. Acad Sci. USA* 86:6572–6576 (1989).
Bruns, R.F., "Adenosine Receptors" *Ann. N.Y. Sci.* 603:211–226 (1990).
Cronstein, B.N. et al., "Neutrophil Adherence to Endothelium is Enhanced via Adenosine $A_1$ Receptors and Inhibited via Adenosine $A_2$ Receptors" *J. Immunol.* 148:2201–2206 (1992).
Cronstein, B.N. et al., "Methotrexate inhibits neutrophil function by stimulating adenosine release from connective tissue cells" *Proc. Natl. Acad. Sci. USA* 88:2441–2445 (1991).
Cronsterin, B.N. et al., "The Adenosine/Neutrophil Paradox Resolved: Human Neutrophils Possess Both $A_1$ and $A_2$ Receptors that Promote Chemotaxis and Inhibit $O_2$ Generation, Respectively", *J. Clin. Invest.* 85:1150–1157 (1990).
Cronstein, B.N. et al., "Adenosine: an Endogenous Inhibitor of Neutrophil–Mediated Injury to Endothelial Cells" *J. Clin. Invest.* 78:760–770 (1986).
Cronstein, B.N. et al., "Adenosine; A Physiologic Modulator of Superoxide Anion Generation by Human Neutrophils. Adenosine Acts Via and $A_2$ Receptor on Human Neutrophils" *J. Immuno.* 135:1366–1371 (1985).
Cronstein, B.N. et al., "Adenosine: A Physiologic Modulator of Superoxide Anion Generation by Human Neutrophils" *J. Exp. Med.* 158:1160–1177 (1983).

Iannone, M.A. et al., "Human Neutrophils Possess Adenosine $A_2$ Receptors", *Fed. Proc.* 44:580 (abstr.) (1985).
Jacobson, K.A. et al., "Adenosine Receptors: Pharmacology, Structure—Activity relationships, and Therapueutic Potential" *J. Med. Chem.* 35:407–422 (1992).
Jarvis, M.F. et al., "[$^3$ H]CGS 2160, A Selective $A_2$ Adenosine Receptor Agonist Directly Labels $A_2$ Receptors in Rat Brain" *J. Pharmacol. Exp. Ther.* 251:888–893 (1989).
Joseph, J. et al., "Exogenous ATP Causes the Contraction of Intact Fibroblasts in Vitro" *Exp. Cell Res.* 176:1–12 (1988).
Kartha, S. et al., "Adenine Nucleotides Stimulate Migration in Wounded Cultures of Kidney Epithelial Cells" *J. Clin. Invest* 90:288–292 (1992).
Meininger, C.J. et al., "Adenosine and Hypoxia Stimulate Proliferation and Migration of Endothelial Cells" *Amer J. Physiol.* 255:3 pt 2:H554–562 (1988).
Olah, M.E. et al., "Adenosine Receptors" *Annu. Rev. Physiol* 54:211–225 (1992).
Ramkumar, V. et al., "Adenosine Receptor: Clinical Implications and Biochemical Mechanisms", *Prog. Drug Res.* 32:195–247 (1988).
Roberts, P.A. et al., "Inhibition by Adenosine of Reactive Oxygen Metabolite Production by Human Polymorphonuclear Leucocytes" *Biochem. J.* 227:669–674 (1985).
Rose, F.R. et al., "Adenosine Promotes Neutrophil Chemotaxis" *J. Exp. Med.* 167:1186–1194 (1988).
Salmon, J.E., "Fcγ Receptor–Mediated Functions in Neutrophils Are Modulated by Adenosine Receptor Occupancy", *J. Immunol.* 145:2235–2240 (1990).
Schrier, D.J. et al., "The Effects of Adenosine Agonists on Human Neutrophil Function" *J. Immunol.* 137:3284–3289.
Stiles, G.L., "Adenosine Receptors: Structure, Funtion and Regulation", *Trends in Pharmacol. Sci.* 7:486–490 (1986).
Stiles, G.L., 1992 "Adenosine Receptors" *J. Biol. Chem.* 267:6451–6464 (1992).
Medline, 89286609 (1989) (Cited by PTO, Dec. 23, 1993, see paper 5).
Chem Abstracts 1975:433057, Zander.
Derwent Abstracts 75–21132W, Zander, 1975.

*Primary Examiner*—Samuel Barts
*Attorney, Agent, or Firm*—Shmuel Livnat; Rader, Fishman & Grauer

[57] ABSTRACT

Agonists of the adenosine $A_2$ receptor promote the migration of endothelial cells, fibroblasts and epithelial cells. Thus, methods and pharmaceutical compositions useful for treating wounds and promoting wound healing comprise agents which cause stimulation of the adenosine $A_2$ receptor, preferably receptor agonists and adenosine uptake blockers. Preferred agonists include 2-phenylaminoadenosine, 2-para-2-carboxyethylphenyl-amino-5'N-ethylcarboxamidoadenosine, 5'N-ethylcarboxamidoadenosine, 5'N-cyclopropyladenosine, 5'N-methylcarboxamidoadenosine and PD-125944. Preferred uptake blockers include dipyridamole, nitrobenzylthio-inosine, dilazep and R75231.

4 Claims, 4 Drawing Sheets

ADENOSINE RECEPTOR AGONISTS FOR THE PROMOTION OF WOUND HEALING

This application is a continuation application Ser. No. 08/046,297, filed Apr. 15, 1993, now abandoned.

INTRODUCTION

The present invention relates to methods for treating wounds and promoting wound healing using agents which cause stimulation of the adenosine $A_2$ receptor, preferably receptor agonists and adenosine uptake blockers.

BACKGROUND OF THE INVENTION

ADENOSINE AND ADENOSINE RECEPTORS

Adenosine is a nucleoside with wide distribution in the body. Adenosine mediates a broad array of physiological responses, including central nervous system sedation, inhibition of platelet aggregation and vascular smooth muscle vasodilatation. These effects occur largely through interaction of adenosine with one of two types of adenosine receptors.

Adenosine receptors comprise a group of cell surface molecules that mediate the physiologic effects of adenosine. (For recent reviews, see Stiles, G. L., *Trends in Pharmacol. Sci.* 7:486–490 (1986); Ramkumar, V. et al.,*Prog. Drug Res.* 32:195–247 (1988); Olah, M. E. et al., *Annu. Rev. Physiol.* 54:211–225 (1992); Stiles, G. L., *J. Biol. Chem.* 267:6451–6454 (1992); Jacobson, K. A. et al., *J. Med. Chem.* 35:407–422 (1992)). This family of receptors was originally classified as $P_1$ or $P_2$ purinergic receptors, depending on their preferential interactions with adenosine ($P_1$) or ATP ($P_2$) (Burnstock, G., In: *CELL MEMBRANE RECEPTORS FOR DRUGS AND HORMONES,* Straub et al., eds., Raven Press, New York, 1978, pp. 107–118). The $P_1$ sites were further subdivided into $A_1$ and $A_2$ adenosine receptors based on their differential selectivity for adenosine analogues (Van Calker, D. et al., *J. Neurochem.* 33:999–1005 (1979); Londos, C. et al., *Proc. Natl. Acad. Sci. USA* 77:2552–2554 (1980)). The $A_1$ adenosine receptor, which is inhibitory to adenylyl cyclase, exhibits the potency order (R)-PIA>NECA>(S)-PIA. The $A_2$ adenosine receptor, which is stimulatory to adenylyl cyclase, has a different potency order where NECA>(R)-PIA>(S)-PIA. ((R)-PIA is $N^6$-(R)-phenylisopropyladenosine; (S)-PIA is $N^6$-(S)-phenylisopropyladenosine; NECA is N-ethyladenosine-5'-uronic acid) Both the $A_1$ and $A_2$ adenosine receptors are widely distributed in the central nervous system and peripheral tissues (Ramkumar, V. et al., supra).

Until relatively recently, no truly useful radioligand was available for characterizing the $A_2$ adenosine receptor. Demonstration of adenosine receptors in smooth muscle was made primarily by functional assays, for example, adenosine stimulation of adenylyl cyclase activity via $A_2$ receptors in vascular smooth muscle cells in culture (Anand-Srivastava, M. B. et al., *Biochem. Biophys. Res. Comm.* 108:213–219 (1982); Anand-Srivastava, M. B. et al.,*Life Sci.* 37:857–867 (1985)). However, the concentrations of adenosine required to elevate cAMP were higher than those required for full vasorelaxation in vivo (Berne, R. M., *Circ. Res.* 47:807–813 (1980); Herlihy, J. T. et al., *Am. J. Physiol.* 230:1239–1243 (1976)). One cell line which has proved useful for study of $A_1$ and $A_2$ adenosine receptors (Ramkumar, V. et al., *Molec. Pharmacol.* 37:149–156 (1990)) is the DDT1 MF-2 line, a smooth muscle cell line derived from a steroid-induced leiomyosarcoma of the vas deferens of an adult Syrian hamster (Norris, J. S. et al., *Nature* 248:422–424 (1974)).

Recently, two compounds were found to be selective high affinity agonist radioligands for the $A_2$ receptor: [$^3$H]CGS 21680 (Jarvis, M. F. et al., *J. Pharmacol. Exp. Ther.* 251:888–893 (1989)) and $^{125}$I-PAPA-APEC, the full chemical name of which is (2-[4-[2-[2-[(4-aminophenyl) methylcarbonyl-amino]ethylaminocarbonyl]ethyl]phenyl] ethylamino-5'-N-ethylcarboxamidoadenosine (Barrington, W. W. et al., *Proc. Natl. Acad. Sci. USA* 86:6572–6576 (1989)). Use of such ligands allowed identification of the $A_2$ binding subunit as a 45 kDa protein (on SDS-PAGE) that was clearly distinguishable from the 38 kDa $A_1$ binding subunit. Use of the azide derivative of $^{125}$I-PAPA-APEC, a direct photoaffinity probe for the $A_2$ receptor, allowed demonstration that the $A_2$ binding subunit is a glycoprotein clearly different from the $A_1$ receptor glycoprotein (Barrington, W. W. et al., *Mol. Pharmacol.* 38:177–183 (1990)). The $A_2$ adenosine receptor has a single carbohydrate chain of either the complex or high mannose type.

Useful adenosine receptor agonists, in particular those with selectivity for the $A_2$ receptor are well-known in the art. These include 2-substituted adenosine-5'-carboxamide derivatives (Hutchison, U.S. Pat. Nos. 4,968,697 and 5,034,381) and N9 cyclopentyl-substituted adenine derivative (Chen et al., U.S. Pat. No. 5,063,233). The above patents are hereby incorporated by reference in their entirety.

Adenosine and its analogues interact with neutrophils in inflammatory responses. While neutrophils are essential for limiting the spread of infection by a variety of microbes, stimulated neutrophils may damage injured tissues while en route to sites of infection or inflammation. Release of adenosine is one mechanism by which normal cells may protect themselves from activated neutrophils. Thus, one important action of adenosine and its analogues is the inhibition of generation of toxic oxygen products, including $O_2^-$ and $H_2O_2$, by interacting with $A_2$ receptors on the neutrophil (Cronstein, B. N. et al., *J. Immunol.* 135:1366–1371 (1985); Roberts, P. A. et al., *Biochem. J.* 227:669–674 (1985); Schrier, D. J. et al., *J. Immunol.* 137:3284–3289); Iannone, M. A. et al., *Fed. Proc.* 44:580 (abstr.) (1985)). Adenosine promotes neutrophil chemotaxis via the same receptor (Cronstein, B. N. et al., supra; Rose, F. R. et al.,*J. Exp. Med.* 167:1186–1194 (1988)). Adenosine receptor ligation regulates inflammatory responses of neutrophils triggered by immune complexes acting through the Fcγ receptor (Salmon, J. E. *J. Immunol.* 145:2235–2240 (1990)). Specifically, activation of $A_2$ receptors inhibited these inflammatory responses, whereas activation of $A_1$ receptors was stimulatory. These authors noted an important role for adenosine at picomolar concentrations as a promoter, and at micromolar concentration as an inhibitor, of neutrophil responses elicited by immune complexes.

Interestingly, the immunosuppressive drug methotrexate, at low concentrations, acts as an antiinflammatory agent at least in part due to its capacity to induced adenosine release by connective tissue cells such as dermal fibroblasts or umbilical vein endothelial cells. The released adenosine interacted with the neutrophil adenosine receptors (Cronstein, B. N. et al., *Proc. Natl. Acad. Sci. USA* 88:2441–2445 (1991)).

The nonselective adenosine receptor agonist, 2-chloroadenosine inhibited adherence of stimulated neutrophils to endothelium, thus protecting the endothelium from inflammatory effects (Cronstein, B. N. et al.,*J. Clin. Invest.* 78:760–770 (1986)). More recently, work from the present inventors' laboratory has demonstrated that occupancy of $A_2$ receptors inhibits neutrophil adherence and generation of toxic metabolites, thus contributing to an anti-inflammatory function (Cronstein, B. N. et al., *J. Immunol.* 148:2201–2206 (1992)).

Thus, work largely from the present inventor's laboratory has led to an emerging picture of adenosine as a unique "autacoid" of inflammation that regulates the accumulation of neutrophils at sites of inflammation. While neutrophils traverse through acellular connective tissue, the low concentrations of adenosine present promote phagocytosis, migration and adherence to some, but not other, surfaces. Near foci of tissue injury, damaged cells release higher concentrations of adenosine that inhibit neutrophil adherence to cells and connective tissue substrata as well as inhibiting production of toxic oxygen metabolites by stimulated neutrophils. Thus adenosine may promote accumulation of neutrophils at sites of tissue injury or microbial invasion, a pro-inflammatory function, but may also act as a feedback regulator of inflammation at sites of tissue damage, an anti-inflammatory function (Cronstein et al., 1992, supra).

Studies by others showed that adenosine itself promoted migration of renal epithelium (Kartha, S. et al., *J. Clin. Invest.* 90:288–292 (1992) and vascular endothelium (Meininger, C. J. et al., *Amer. J. Physiol.* 255:3 pt 2:H554–562 (1988). This latter reference suggested that the effect of adenosine on chemotaxis may be mediated by a receptor (of unknown or unspecified type).

WOUND HEALING

Wound healing requires a coordinated influx of fibroblasts, vascular endothelium and epithelium. There is clearly a recognized need in the art for new agents and methods which promote wound healing. Agents which promote a more rapid influx of fibroblasts, endothelial and epithelial cells into wounds should increase the rate at which wounds heal. Agents useful in treating wound healing can be identified and tested in a number of in vitro and in vivo models.

In vitro systems model different components of the wound healing process, for example the return of cells to a "wounded" confluent monolayer of tissue culture cells, such as fibroblasts (Verrier, B. et al., *EMBO J.* 5:913–917 (1986)), endothelial cells (Miyata, K. et al., *Jpn. J. Opthalmol.* 34:257–266 (1990)) or epithelial cells (Kartha, S. et al., *J. Clin. Invest.* 90:288–292 (1992)). Other systems permit the measurement of endothelial cell migration and/or proliferation (Muller, G. et al., *Proc. Natl. Acad. Sci. USA* 84:5600–5604 (1987); Sato, Y. et al., *J. Cell Biol.* 107:1199–1205 (1988)).

In vivo models for wound healing are also well-known in the art, including wounded pig epidermis (Ohkawara, A. et al., In: BIOCHEMISTRY OF CUTANEOUS EPITHELIAL DIFFERENTIATION, Seiji et al., eds., University Park Press, Baltimore, 1977, pp. 274–278) or drug-induced oral mucosal lesions in the hamster cheek pouch (Cherrick, H. M. et al., *J. Invest. Dermatol.* 63: 284–286 (1974).

No information is available regarding the treatment of wounds with compounds active at adenosine receptors. This is the subject matter of the present invention.

SUMMARY OF THE INVENTION

The present inventors and their colleagues have shown, in in vitro studies, that adenosine receptor agonists promote the migration of endothelial cells and fibroblasts. On this basis, they conceived of the use of adenosine receptor agonists, or compounds which raise the level of adenosine available to these receptors, to treat wounds and promote wound healing. The methods of the present invention are useful for the treatment of any of a number of type of wounds, including, but not limited to, wounds caused by burns, ischemic and decubitus ulcers or ulcers due to infectious and inflammatory processes.

Thus, the present invention is directed to a method for treating a wound in a subject, comprising administering to the subject at least one agent which causes stimulation of the adenosine $A_2$ receptor. Administration is preferably by the topical route.

Also provided is a method for treating a wound in a subject, comprising administering to the subject at least one agent which causes stimulation of the adenosine $A_2$ receptor, in combination with a medicament selected from the group consisting of an antibacterial agent, an antiviral agent, an antifungal agent, an antiparasitic agent, an antiinflammatory agent, an analgesic agent, an antipruritic agent, or a combination thereof.

In another embodiment, the present invention provides a method for stimulating the influx of fibroblasts, vascular endothelial cells or epithelial cells into a wound, which method comprises contacting the fibroblasts, vascular endothelial cells, epithelial cells, or a combination thereof with an agent which causes stimulation of the adenosine $A_2$ receptor on any of the cells.

In the above methods, the agent is preferably an adenosine $A_2$ receptor, agonist or an inhibitor of adenosine uptake.

An adenosine $A_2$ receptor agonist useful in the above methods is preferably selected from the group consisting of adenosine, 2-phenylaminoadenosine, 2-para-2-carboxyethylphenylamino-5'N-ethylcarboxamidoadenosine, 5'N-ethylcarboxamidoadenosine, 5'N-cyclopropyladenosine, 5'N-methylcarboxamidoadenosine and PD-125944 (for chemical structure, see Bruns, R. F., Ann. N.Y. Acad. Sci. 603:211–226 (1990) at page 216).

An adenosine uptake inhibitor useful in the above methods is preferably selected from the group consisting of dipyridamole, nitrobenzylthioinosine, dilazep and R75231.

The present invention is further directed to a pharmaceutical composition for treatment of a wound, comprising:

(a) at least one agent which causes stimulation of the adenosine $A_2$ receptor; and (b) a pharmaceutically acceptable carrier or excipient preferably for topical use.

The pharmaceutical composition may further comprise:

(c) a medicament selected from the group consisting of an antibacterial agent, an antiviral agent, an anti-fungal agent, an anti-parasitic agent, an anti-inflammatory agent, an analgesic agent, an anti-pruritic agent, and a combination thereof.

In the above pharmaceutical compositions, the at least one agent is preferably an adenosine $A_2$ receptor agonist or an inhibitor of adenosine uptake. The adenosine $A_2$ receptor agonist is preferably selected from the group consisting of adenosine, 2-phenylaminoadenosine, 2-para-2-carboxyethylphenyl-amino-5'N-ethylcarboxamidoadenosine, 5'N-ethylcarboxamidoadenosine, 5'N-cyclopropyladenosine, 5'N-methylcarboxamidoadenosine and PD-125944.

In the above pharmaceutical compositions, the adenosine uptake inhibitor is preferably selected from the group consisting of dipyridamole, nitrobenzylthioinosine, dilazep and R75231.

DETAILED DESCRIPTION OF THE INVENTION

The present inventors have conceived of the use of adenosine, an adenosine $A_2$ receptor agonist or an adenosine uptake blocker, to promote the healing of wounds.

Occupancy of adenosine $A_1$ and $A_2$ receptors on the surface of vascular endothelium, fibroblasts, epithelium and leukocytes promotes the migration of these cells. Specific adenosine receptor antagonists block the receptor-mediated effects of the agonists, observed as diminished migration of fibroblasts, epithelium, endothelium and leukocytes.

Thus, the present invention provides methods useful for promoting wound healing, which comprise treating a wound, or a subject having a wound, with an agonist active at the adenosine $A_2$ receptor or with a pharmaceutical composition comprising such an agonist.

According to the present invention, the fact that a candidate adenosine receptor agonist promotes wound healing via its action at the adenosine receptor may be verified by showing that the increased rate of wound healing induced by the agonist is diminished to control levels by the presence of an adenosine receptor antagonist. Thus, for purposes of testing a potential adenosine $A_2$ receptor agonist compound and understanding its mode of action, adenosine receptor antagonists have utility. Methods for utilizing such antagonists for the analysis of the wound healing activity of an agonist are provided herein.

Also included in the present invention are methods for promoting wound healing, which methods comprise administering to a wound or to a subject having a wound, an adenosine uptake blocker. Such uptake blockers raise extracellular levels of adenosine which has been released from cells and tissues. By doing so, they increase the availability of adenosine to interact with adenosine receptors on cells in the vicinity, thereby mimicking receptor agonists. Antagonists at adenosine receptors therefore counteract the effect of adenosine uptake blockers, just as they do with receptor agonists, thereby inhibiting migration of fibroblasts, endothelium and leukocytes induced by an adenosine uptake blocker.

Useful adenosine uptake inhibitors according to the present invention include dipyridamole and nitrobenzylthioinosine, dilazep, and R75231 (Janssen Pharmaceuticals). Dipyridamole, for example, is currently in pharmaceutical use in oral and intravenous form. The pharmacological effects of dipyridamole on platelets and coronary arteries are thought to be mediated by the high concentrations of adenosine which accumulate its presence (e.g., Cronstein, B. N. et al., J. Exp. Med. 158:1160–1177 (1983)).

Examples of $A_2$ receptor agonists useful in the present invention include, but are not limited to: 2-phenylaminoadenosine (CV-1808), 2-para-2-carboxyethylphenylamino-5'N-ethylcarboxamidoadenosine (CGS-21680) or related compound CGS-21577 (see Bruns, supra, at page 216), 5'N-ethylcarboxamidoadenosine (NECA), 5'N-cyclopropyladenosine, PD-125944, and 5'N-methylcarboxamidoadenosine. For a more complete list of agonists, see Jacobson, K. A. et al., J. Med. Chem. 35:407–422 (1992), which reference is hereby incorporated by reference in its entirety.

$A_2$ receptor antagonists which may be used in conjunction with the agonists to either test the agonist's mode of action or to terminate the agonist's effect, include, but are not limited to 1,3-dipropyl-7-methylxanthine and 3,7-dimethyl-1-propargylxanthine, Useful adenosine $A_1$ agonists for studying the adenosine receptor-related mechanisms involved in wound healing include, but are not limited to, adenosine amine congener, $N^6$-cyclopentyladenosine, 2-chloro-$N^6$-cyclopentyladenosine, $N^6$-cyclohexyladenosine, ENBA, and $N^6$-phenylisopropyladenosine(-))

Adenosine $A_1$ receptor antagonists, which counteract the action of $A_1$ agonists (or the action of adenosine uptake blockers mediated via $A_1$ receptors) include, but are not limited to, 8-cyclopentyl-1,3-dipropylxanthine, 8-cyclopentyl-1,3-dimethylxanthine, and 1,3-diethyl-8-phenylxanthine. For a more complete list of antagonists acting at adenosine $A_1$ and $A_2$ receptors, see Jacobson, K. A. et al., supra.

IN VIVO WOUND HEALING

The effects of adenosine and adenosine receptor agonists and antagonists are tested in animal models of wound healing, preferably in rats and pigs, to determine whether a particular adenosine $A_2$ receptor agonist improves the quality, rate or extent of wound healing. Such an improvement in wound healing is thought to occur via occupancy of adenosine $A_2$ receptors on inflammatory cells (macrophage/monocytes, neutrophils), fibroblasts, vascular cells (endothelium) and dermal epithelial cells similar to the effects reported in in vitro studies, although the present inventors do not wish to be bound by this proposed mechanism of action.

The effects of specific adenosine $A_1$ and $A_2$ receptor agonists are tested in conjunction with receptor-specific antagonists to verify the action of the agonist.

SMALL ANIMAL MODEL: RATS

In a preferred model, a thermal wound of uniform size, for example, 1 cm×1 cm, is induced on the back of ether-anesthetized rats, such as 12-week old Fisher rats, by use of an iron of appropriate size which has been heated with a flame of a Bunsen burner.

Following induction of the wound, medium alone, adenosine or an adenosine receptor-specific agonist or antagonist is applied to the wound. The adenosine receptor agonist, antagonist or medium is reapplied twice daily. At the end of two days one group of animals is sacrificed and the wounds excised for histological analysis. In other group of animals, the wounds are treated for four to six days, the animals sacrificed and the wounds excised for histologic analysis.

After appropriate fixation, sectioning and staining, the wounds are examined for:
(1) the presence and extent of migration into the wound of fibroblasts, blood vessels and epithelial cells, observed as the formation of granulation tissue. A subjective scale of 0–4 may be used to score the reactions; and
(2) the presence of inflammatory cells (neutrophils, lymphocytes and mononuclear cells), which may be scored using a subjective scale of 0–4.

The individual examining the wound histology is preferably blinded to the source of the tissue or the treatment administered to the wound.

Each treatment group, including a control of carrier alone, preferably comprises 6–8 animals.

LARGE ANIMAL MODEL: PIGS

Tests similar to those described above for rats are performed in large animals, preferably pigs. The wound is created by excising a 3 cm×3 cm area of epidermis and dermis under anesthesia. The test compounds are then applied, as above, twice per day and the wound excised after 2, 4, or 14 days for histologic analysis, as described above. Smaller groups of animals are generally used in these studies (3–5 animals per treatment group).

If a given adenosine receptor agonist or adenosine uptake blocker promotes wound healing then one will observe, relative to controls:

(1) fewer leukocytes (neutrophils and monocytes) in the wound; and
(2) increased numbers of fibroblasts, blood vessels and epithelium in the healing wound.

IN VITRO WOUND ASSAYS

In a preferred embodiment, wound assays are performed as described by Shleef et al., Tissue Cell 14:629–636 (1982). Cells, for example, human umbilical or saphenous vein endothelial cells, dermal fibroblasts, etc., are cultured in Medium 199 containing in 10% fetal bovine serum until they form confluent monolayers, for example, in 12 well culture plates. The confluent monolayers were wounded with a razor blade after 60 minutes of treatment with mitomycin C (10 $\mu$g/ml). The cells are rinsed several times and the test compounds are added to replicate wells. Cell migration into the wound is assessed at various times thereafter by phase contrast microscopy using an inverted microscope. Quantitation may be performed by aligning the original edge of the wound with the "0" line on a 10×10 grid-reticle and the number of cells in each of the 10 rows defined by the reticle are counted.

Wound assays may also be performed as described by Sato et al., 1988, supra). Briefly, confluent monolayers of endothelial cells, for example human umbilical vein endothelial cells or bovine aortic endothelial cells, growing in 35 mm dishes are washed with phosphate-buffered saline (PBS), wounded with a razor blade, and washed again with PBS. The cells are incubated in medium, preferably AMEM, containing 0.1% bovine serum albumin for about 20 hr at 37° C., and the cells are fixed preferably with absolute methanol and stained with Giemsa stain. Cells that migrate from the edge of the wound are counted in successive 125 $\mu$m increments at 100× using a light microscope with an ocular grid. Several, preferably at least six, different fields, are counted and the mean cell number is determined.

The adenosine receptor-acting compound is added at the desired range of concentrations and analyzed for its effects on cell migration relative to an appropriate control vehicle.

PHARMACEUTICAL COMPOSITIONS AND FORMULATIONS

The preferred animal subject of the present invention is a mammal. By the term "mammal" is meant an individual belonging to the class Mammalia. The invention is particularly useful in the treatment of human subjects.

By the term "treating" is intended the administering to a subject of an adenosine $A_2$ receptor agonist for purposes of treating a wound and for promotion of wound healing.

Provided herein is a pharmaceutical composition comprising an amount of at least one adenosine $A_2$ receptor agonist effective in treating a wound or in promoting wound healing. In another embodiment, the pharmaceutical composition further includes a second medicament in combination with the at least one adenosine $A_2$ receptor agonist. Preferred second medicaments include any agents which are known to promote wound healing or to treat problems or symptoms associated with wounds. Examples of such agents include disinfectants such as antibacterial agents or antiviral agents, anti-inflammatory agents, agents which induce relief from pain or itching, and the like.

Medicaments are considered to be provided "in combination" with one another if they are provided to the patient concurrently or if the time between the administration of each medicament is such as to permit an overlap of biological activity. In one preferred embodiment, the adenosine $A_2$ receptor agonist and the second medicament comprise a single pharmaceutical composition.

The pharmaceutical compositions of the present invention comprising an adenosine $A_2$ receptor agonist may be administered by any means that achieve their intended purpose. Amounts and regimens for the administration of the pharmaceutical composition can be determined readily by those with ordinary skill in the clinical art of treating wounds.

Preferred administration is by the topical route. However, alternatively, or concurrently, the agent may be administered by parenteral, subcutaneous, intravenous, intramuscular, intraperitoneal or transdermal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the adenosine $A_2$ receptor agonist or adenosine uptake blocker is contained in an amount effective to achieve its intended purpose. While individual needs vary, determination of optimal ranges of effective amounts of each component is within the skill of the art. Typical dosages comprise 0.01 to 100 mg/kg/body wt. The preferred dosages comprise 0.1 to 100 mg/kg/body wt. The most preferred dosages comprise 1 to 100 mg/kg/body wt.

For topical application, which is particularly important in treating a wound, the adenosine $A_2$ receptor agonist or adenosine uptake blocker of the present invention may be incorporated into topically applied vehicles such as salves or ointments, which have both a soothing effect on the skin as well as a means for administering the active ingredient directly to the affected area. Preferred vehicles include Shephard's® Cream, Aquaphor® and Cetaphil® lotion.

The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000), conventional creams such as HEB cream, gels, as well as petroleum jelly and the like.

Also suitable for topic application are sprayable aerosol preparations wherein the active ingredient, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the active compounds of the present invention.

For the preferred topical applications, especially for treatment of humans and animals having a wound, it is preferred to administer an effective amount of a compound according to the present invention to the wounded area, e.g., skin surfaces. This amount will generally range from about 0.001 mg to about 1 g per application, depending upon the area to be treated, the severity of the symptoms, and the nature of the topical vehicle employed. A preferred topical preparation is an ointment wherein about 0.01 to about 50 mg of active ingredient is used per ml of ointment base, such as PEG-1000.

Other pharmaceutically acceptable carriers for the adenosine $A_2$ receptor agonist or adenosine uptake blocker according to the present invention are liposomes, pharmaceutical compositions in which the active ingredient is contained either dispersed or variously present in corpuscles consisting of aqueous concentric layers adherent to lipidic layers. The active ingredient may be present both in the aqueous layer and in the lipidic layer, inside or outside, or, in any event, in the non-homogeneous system generally known as a liposomic suspension.

The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

The compounds may also be formulated for transdermal administration, for example, in the form of transdermal patches so as to achieve systemic administration.

Pharmaceutical compositions given by routes other than the topical route preferably contain, in addition to the pharmacologically active compound, suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 20 to 75 percent of active compound(s), together with the excipient.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension include, for example, sodium carboxymethyl cellulose, sorbitol, and/or dextran. Optionally, the suspension may also contain stabilizers.

The pharmaceutical formulation for systemic administration according to the invention may be formulated for enteral, parenteral or topical administration. Indeed, all three types of formulation may be used simultaneously to achieve systemic administration of the active ingredient.

Suitable formulations for oral administration include hard or soft gelatin capsules, dragees, pills tablets, including coated tablets, elixirs, suspensions, syrups or inhalations and controlled release forms thereof.

Suitable injectable solutions include intravenous subcutaneous and intramuscular injectable solutions. The adenosine $A_2$ receptor agonist or adenosine uptake blocker may also be administered in the form of an infusion solution or as a nasal inhalation or spray.

ADENOSINE RECEPTOR BINDING ASSAYS

Any of a number of ligand binding assays well-known in the art may be utilized to test whether a particular agent suspected of being an adenosine $A_2$ receptor agonist indeed binds to the receptor and mediates the expected biochemical or biological activity, such as stimulation of adenylyl cyclase activity. Such assays of radioligand binding and measurement of agonist induced biochemical changes are disclosed in a number of references, for example, Van Calker, D. et al., *J. Neurochem.* 33:999–1005 (1979) and Stiles, G. L., *Trends in Pharmacol. Sci.* 7:486–490 (1986); Ramkumar, V. et al., supra; Olah, M. E. et al., supra; Stiles, G. L., 1992, supra; Jacobson, K. A. et al., supra.

A well-known assay method is based on using a ligand or agonist which is capable of binding to and activating both the $A_1$ and $A_2$ subtypes of adenosine receptors. In this approach, a displacer compound which occupies any adenosine $A_1$ receptors in a preparation is used which leaves $A_2$ receptors available for binding and activation (Bruns, U.S. Pat. No. 4,705,758, which reference is hereby incorporated by reference).

Having now generally described the invention, the same will be more readily understood through reference to the following examples which are provided by way of illustration, and are not intended to be limiting of the present invention, unless specified.

EXAMPLE: STIMULATION OF ENDOTHELIAL CELL AND FIBROBLAST MIGRATION BY AN $A_2$ ADENOSINE RECEPTOR AGONIST

A poorly metabolized $A_2$ adenosine receptor agonist, 5'N-ethylcarboxamidoadenosine (NECA), was tested for its ability to promote endothelial cell migration, a key step in the neovascularization of a wound and wound healing.

Cells, either human umbilical or saphenous vein endothelial cells, dermal fibroblasts, or smooth muscle cells, were cultured and allowed to grow into confluent monolayers in 12 well plates. The confluent monolayers were wounded with a razor blade as described by Shleef and Birdwell (*Tissue Cell* 14:629–636 (1982) after 60 minutes of treatment with mitomycin C (10 μg/ml). The cells were rinsed twice with saline before the test materials were added to duplicate or triplicate wells. Cell migration into the wound was assessed at various times thereafter by phase contrast microscopy. The original edge of the wound was aligned with the "0" line on a 10×10 grid-reticle and the number of cells in each of the 10 rows defined by the reticle were counted.

Figure 1:
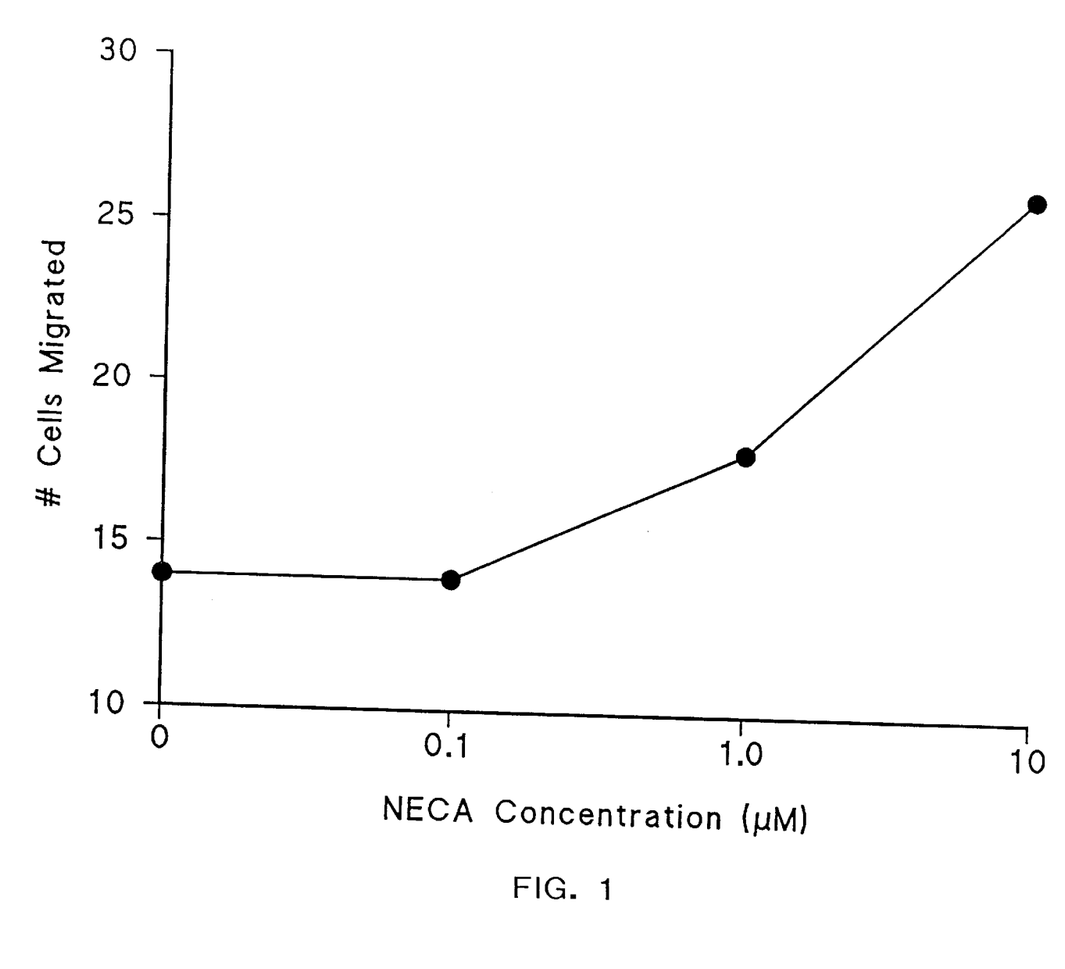
FIG. 1 is a graph showing that an adenosine $A_2$ receptor agonist, 5'N-ethylcarboxamidoadenosine (NECA), promotes migration of human umbilical vein endothelial cells after 18 hours.

FIG. 1 presents results of a representative experiment (of three) which tested the effects of NECA on the migration of human umbilical vein endothelial cells after 18 hours of treatment. Each point represents the mean of three replicate wells. The results indicate a significant promotion of endothelial cell migration by this agonist. The approximate $EC_{50}$ of NECA for enhanced endothelial cell migration in this experiment was 2 µM. In other experiments, the EC50 ranged from 0.1 to 2 µM.

Figure 2:
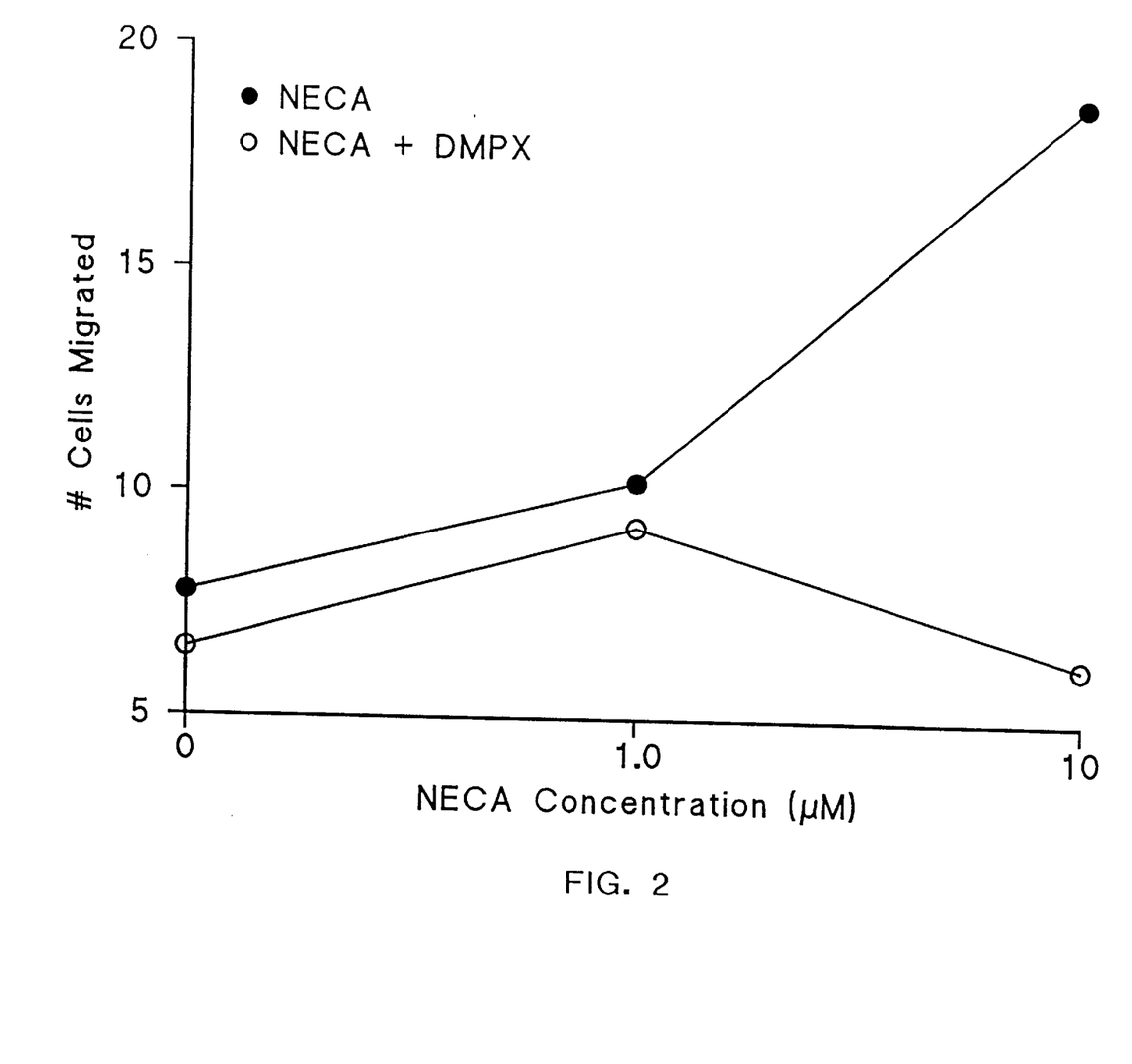
FIG. 2 is a graph showing that NECA promotes migration of human saphenous vein endothelial cells, and that this effect is diminished by the adenosine $A_2$ receptor antagonist, 3,7-dimethylpropargylxanthine (10 μM).

FIG. 2 presents results of a representative experiment (of three) which tested the effects of NECA on the migration of human saphenous vein endothelial cells after 72 hours of treatment. Each point represents the mean of three replicate wells. The results again show a significant promotion of endothelial cell migration by this agonist. Inclusion in the incubation of the adenosine $A_2$ receptor antagonist, 3,7-dimethylpropargylxanthine at 10 µM inhibited the effect of NECA. This result argues that the effect of NECA was required its binding to the adenosine $A_2$ receptor.

In other experiments, the adenosine $A_1$ receptor agonist, $N^6$-cyclopentyladenosine (CPA) was tested for its ability to alter endothelial cell migration. The results are shown in Table I, below. No effect on migration was observed.

TABLE I

EFFECT OF $N^6$-CYCLOPENTYLADENOSINE (CPA) ON MIGRATION OF HUMAN UMBILICAL VEIN ENDOTHELIAL CELLS

| CPA (nM) | # Cells Migrated |
| --- | --- |
| 0 | 9.8 ± 1.0 |
| 0.1 | 10.0 ± 3.6 |
| 1.0 | 9.5 ± 7.2 |
| 10.0 | 10.8 ± 3.5 |

Figure 3:
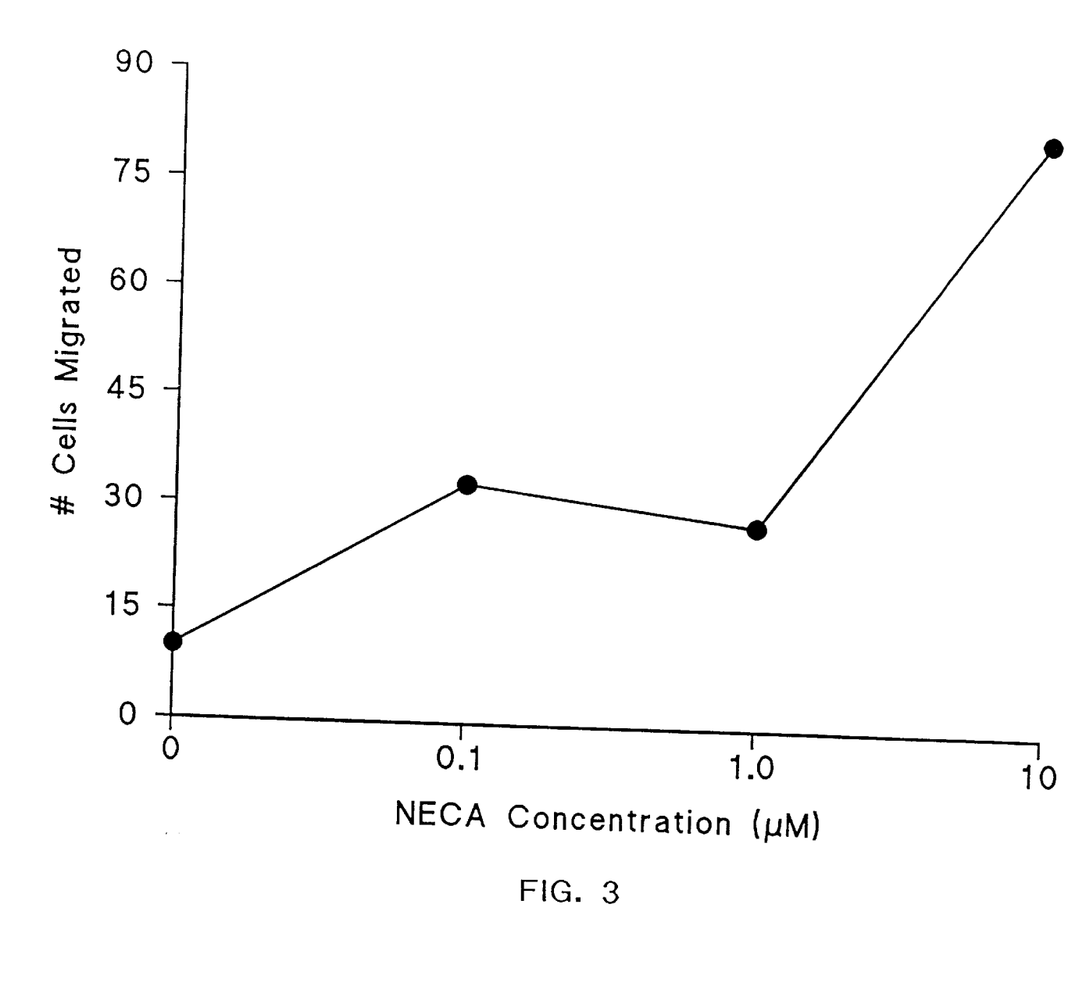
FIG. 3 is a graph showing that NECA promotes migration of fibroblasts.

The enhanced migration induced by NECA was not limited to endothelial cells. FIG. 3 shows the results of a representative experiment (of two) which tested the effect of NECA of fibroblast migration after 48 hours. Each point represents the mean of three replicate wells. The results show a significant promotion of fibroblast migration by NECA.

Figure 4:
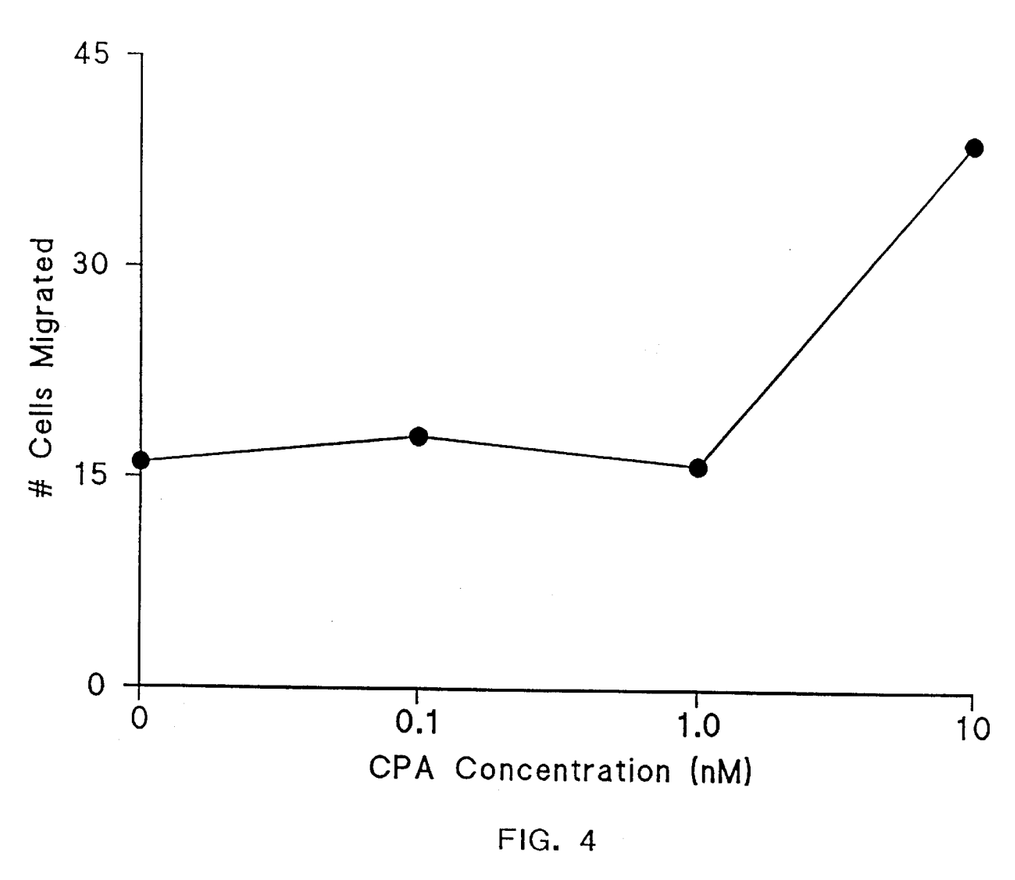
FIG. 4 is a graph showing that the adenosine $A_1$ receptor agonist, $N^6$-cyclopentyladenosine (CPA) promotes migration of fibroblasts.

While CPA did not enhance migration of endothelial cells, it did show some effect on fibroblast migration. FIG. 4 shows the results of a representative experiment (of two) indicating stimulation of fibroblast migration after 24 hours by CPA. These results are consistent with the notion that adenosine $A_1$ receptor agonists may promote migration of some cell types.

The effects of the adenosine receptor agonists on cell migration were further shown to be selective for particular cell types. Thus neither NECA nor CPA stimulated migration by smooth muscle cells (Table II, below.

TABLE II

EFFECT OF ADENOSINE ANALOGUES ON MIGRATION OF SMOOTH MUSCLE CELLS

| Agent | Conc. | # Cells Migrated |
| --- | --- | --- |
| Control | | 6.5 ± 8.5 |
| NECA | 10 µM | 5.0 ± 7.1 |
| CPA | 10 nM | 6.3 ± 7.4 |

The above findings are in agreement with (1) earlier observations from the present inventors' laboratories that adenosine and its analogues promote neutrophil migration, albeit via the $A_1$ adenosine receptor, and (2) studies by others showing that adenosine promoted migration of renal epithelium and vascular endothelium.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for treating a wound in a subject, comprising administering topically to said wound an adenosine $A_2$ receptor agonist selected from the group consisting of 2-phenylaminoadenosine, 2-{para-(2-carboxyethyl)phenyl}amino-5'N-ethylcarboxamidoadenosine, 5'-N-cyclopropylcarboxamidoadenosine, 5'N-methylcarboxamidoadenosine and PD-125944, in an amount effective to stimulate said receptors of said cells, thereby promoting wound healing.

2. A method according to claim 1 wherein said wound is a burn, an ischemic ulcer, a decubitus ulcer, an ulcer resulting from an infectious process or an ulcer resulting from an inflammatory processes.

3. A method according to claim 1, wherein said topical administration includes, in combination with said agonist, one or more medicaments selected from the group consisting of an antibacterial agent, an antiviral agent, an antifungal agent, an antiparasitic agent, an antiinflammatory agent, an analgesic agent and an antipruritic agent.

4. A method for stimulating the influx of fibroblasts, vascular endothelial cells or epithelial cells into a wound, which method comprises contacting said fibroblasts, vascular endothelial cells or epithelial cells with an adenosine $A_2$ receptor agonist selected from the group consisting of 2-phenylaminoadenosine, 2-{para-(2-carboxyethyl)phenyl}amino-5'N-ethylcarboxamidoadenosine, 5'-N-cyclopropylcarboxamidoadenosine, 5'N-methylcarboxamidoadenosine and PD-125944, which agonist stimulates adenosine $A_2$ receptors on any of said cells, thereby stimulating said influx.

* * * * *